(12) United States Patent
Malmqvist-Granlund et al.

(10) Patent No.: US 6,391,340 B1
(45) Date of Patent: May 21, 2002

(54) DRY POWDER PHARMACEUTICAL FORMULATION

(75) Inventors: Karin Malmqvist-Granlund, Kävlinge; Gordon Santesson, Hörby; Eva Trofast, Lund, all of (SE)

(73) Assignee: AstraZeneca AB, Södertälje (SE)

( * ) Notice: Subject to any disclaimer, the term of this patent is extended or adjusted under 35 U.S.C. 154(b) by 0 days.

(21) Appl. No.: 09/486,253

(22) PCT Filed: Nov. 3, 1999

(86) PCT No.: PCT/SE99/01990

§ 371 Date: Feb. 24, 2000

§ 102(e) Date: Feb. 24, 2000

(87) PCT Pub. No.: WO00/27373

PCT Pub. Date: May 18, 2000

(30) Foreign Application Priority Data

Nov. 5, 1998 (SE) .............................................. 9803770

(51) Int. Cl.$^7$ .................................................... A61K 9/14
(52) U.S. Cl. ........................ 424/489; 424/434; 514/951
(58) Field of Search .................................. 424/489, 434

(56) References Cited

FOREIGN PATENT DOCUMENTS

| EP | 0496307 A1 | 7/1992 |
| EP | 0648498 A1 | 4/1995 |
| WO | WO 9311746 A1 | 6/1993 |

*Primary Examiner*—James M. Spear
(74) *Attorney, Agent, or Firm*—Fish & Richardson P.C.

(57) ABSTRACT

There is described a solid particulate pharmaceutical formulation suitable for application to the nose comprising finely divided additive particles and finely divided drug particles, wherein the mass median diameter of the drug particles is greater than that of the additive particles.

13 Claims, No Drawings

DRY POWDER PHARMACEUTICAL FORMULATION

This application is a 371 of PCT/SE99/01990 filed Nov. 3, 1999.

This invention relates to a new pharmaceutical formulation and to methods for its preparation and use.

Conditions of the nose, and in particular allergic conditions which effect the nose, occur in an ever increasing proportion of the population. Such conditions are often treated by the administration of appropriate topically active medicines to the nose either by means of pressurised aerosol, liquid (usually aqueous) or dry powder formulations of the required drug. The dry powder formulations are often the same as, or slight modifications of, inhalation formulations of the same drug for use in the treatment of the lung. Such inhalation formulations contain the drug in the form of very fine particles intended to reach deep into the lung.

The very fine particles of the drug used in inhalation formulations are difficult to handle because of the Van der Waal's forces which make them highly cohesive. In order to overcome this the fine particles of drug (optionally in admixture with fine particles of a carrier or diluent) can be agglomerated into larger pellets which are sufficiently large and sufficiently strong to be easily handled, but which are sufficiently weak to break up into the individual fine particles on inhalation. Alternatively the fine particles of drug can be mixed with a coarse carrier to provide a free flowing mixture which again yields the fine particles on inhalation.

When formulations which are designed principally for inhalation are used to treat the nose they are likely to be less than optimal for such treatment, partly because some of the fine particles of drug pass through the nose and reach the pharynx, trachea and lung. This is undesireable in that the portion of drug not remaining in the nose is likely to be ineffective for the treatment of a nasal condition and also may cause unwanted side effects in the other organs.

We have now found that these disadvantages can be overcome by using larger particles of the drug. However the particles of the drug should still be small enough to be dispersed widely over the nasal mucosa.

These larger, but still relatively small, particles are much less cohesive than the very small particles used in inhalation formulations, but they are still generally insufficiently free flowing to enable them to be handled easily in pharmaceutical production, eg on automated machines, or to fill into the dosing chamber of a multidose nasal inhaler, or to spread evenly over the nasal mucosa.

We have now found a means of formulating these larger, but still relatively small particles so that these problems can be overcome.

Thus according to the invention we provide a solid particulate pharmaceutical formulation suitable for application to the nose comprising finely divided additive particles and finely divided drug particles, wherein the mass median diameter of the drug particles is greater than that of the additive particles.

We prefer at least 85% of the drug particles to have a size over 5 µm, and at least 90% a size of less than 20 µm.

We prefer at least 85%, and more preferably at least 70% of the drug particles to have a size below 15 µm.

We prefer at least 90% of the additive particles to be of a size of less than 10 µm.

We further prefer at least 80% of the additive particles to be of a size of less than 7 µm, and more preferably not more than 10% of the additive particles to be of a size of less than 1 µm.

In this specification percentages are by weight, and sizes are measured by conventional means, e.g. by a Coulter counter or by a laser particle size analyser (e.g. Malvern).

The proportion of the additive and the drug will vary according to the particular drug and additive. Thus with a potent drug the proportion of the additive will generally be higher than with a less potent drug. In general we prefer the proportion to be from 99.6 to 0.4, and more preferably from 20 to 0.5, and especially about 1, parts by weight of additive to one part by weight of drug.

The mixture according to the invention may be agglomerated using conventional techniques known per se to produce pellets having a size of from 10 to 2,000, and preferably of from 10 to 1,000 µm. The pellets of the invention contain both drug and additive. The individual components of the mixture may be made of the desired particle size by milling, micronising, sieving, direct synthesis, or by other conventional techniques for the preparation of particles within a desired size range.

The drugs which may be used in the formulations of the invention are those which are conventionally applied to the nose. The drugs may be used for the treatment of conditions of the nose, or may be applied to the nose to have their effect in some other part of the body. Classes of drugs used to treat conditions of the nose include antiallergic drugs, for example antihistamines, e.g. loratidine or terfenadine; anti-inflammatories for example steroids, e.g budesonide (including the 21-(3-sulphopropionate) thereof), ciclesonide, fluticasone, mometasone, tipredane, flumethasone acetonide, triamcinolone acetonide, beclomethasone, RPR-106541, anticholinergic agents, e.g. ipratropium bromide, thiotropium bromide and oxytropium bromide; azelastine, levocabastine, sodium cromoglycate, nedocromil sodium; and vasoconstrictors. Other clases of drugs suitable for use in the invention include proteins, peptides such as insulin, hormones etc. Mixtures of one or more such drugs may also be used. Salts, solvates, hydrates and esters of the above drugs can also be used when such are formed, for example esters of mometasone such as the furoate ester and hydrates thereof. Preferred drugs include budesonide and mometasone particularly in the form of the furoate ester of mometasone and hydrates thereof.

The additive may be a carrier, diluent or other excipient (e.g. an absorption enhancer such as sodium taurocholate, or an antioxidant) which imparts desired properties to the formulation.

The carrier may be any suitable carrier which is acceptable to the nasal mucosa. Such carriers are well known and include carbohydrates and especially sugars, e.g. sucrose. The preferred carrier is lactose, e.g in the form of its monohydrate.

The particles and formulations according to the invention may be administered to the nose using a variety of devices known for the administration of drugs to the nose. We particularly prefer to use the dry powder device known as Turbuhaler®.

The invention is illustrated, but in no way limited, by the following Example.

EXAMPLE

Budesonide and lactose monohydrate were separately micronised using conventional techniques known per se. The budesonide particles (which have optionally been conditioned according to the process of WO95/05805) had a mass median diameter of 7.0 µm and the lactose particles had a mass median diameter of 2.5 µm, and were conditioned as described in WO95/05805. 90 mg of the micronised budesonide was made up to a total weight of 1 g by admixture with the micronised and conditioned lactose and spheronised and sieved using conventional techniques to produce soft pellets of a size of less than 0.8 m.

What is claimed is:

1. A solid particulate pharmaceutical formulation for application to the nose comprising finely divided additive particles and finely divided drug particles, wherein the mass median diameter of the drug particles is greater than that of the additive particles.

2. A formulation according to claim 1, wherein 85% of the drug particles have a size over 5 µm and at least 90% have a size of less than 20 µm.

3. A formulation according to claim 1, wherein at least 90% of the additive particles are of a size of less than 10 µm.

4. A formulation according to claim 3, wherein at least 80% of the additive particles are of a size of less than 7 µm, and not more than 10% of the additive particles are of a size of less than 1 µm.

5. A formulation according to claim 1, wherein the proportion by weight of the additive and the drug is in the range of from 99.6 to 0.4:1.

6. A formulation according to claim 5, wherein the proportion is from 20 to 0.5:1.

7. A formulation according to claim 1, wherein the formulation is in the form of agglomerates of a size from 10 to 2,000 µm.

8. A formulation according to claim 1, wherein the drug is an anti-inflammatory or anti-allergic drug.

9. A formulation according to claim 1, wherein the drug is budesonide.

10. A formulation according to claim 1, wherein the drug is mometasone or the furoate ester of mometasone and hydrates thereof.

11. A formulation according to claim 1, wherein the additive is a carrier.

12. A formulation according to claim 11, wherein the carrier is lactose.

13. A device for the application of a drug to the nose containing a formulation according to claim 1.

* * * * *